United States Patent [19]

Miller, Jr. et al.

[11] 3,944,662
[45] Mar. 16, 1976

[54] NON-VOLATILE SLOW-RELEASE PESTICIDAL GENERATORS

[75] Inventors: Alexander Miller, Jr.; Juan G. Morales, both of Modesto, Calif.

[73] Assignee: Shell Oil Company, Houston, Tex.

[22] Filed: Oct. 7, 1974

[21] Appl. No.: 512,652

Related U.S. Application Data

[63] Continuation-in-part of Ser. No. 244,942, April 17, 1972, abandoned.

[52] U.S. Cl. ............... 424/78; 424/19; 424/219
[51] Int. Cl.² ............... A61K 31/74; A01N 9/36
[58] Field of Search ............... 424/19, 219, 78

[56] References Cited
UNITED STATES PATENTS 3,769,417   10/1973   Van Breen ............... 424/19

FOREIGN PATENTS OR APPLICATIONS 1,040,553   9/1966   United Kingdom

*Primary Examiner*—V. D. Turner

[57] ABSTRACT

Storage stable, slow-release pesticidal generators comprising β-2-chloro-1-(2,4,5-trichlorophenyl)-vinyl dimethyl phosphate dispersed in a matrix of a plasticized thermoplastic resin, said generator being characterized by having on the surface thereof crystals of β-2-chloro-1-(2,4,5-trichlorophenyl)-vinyl dimethyl phosphate in a specified crystalline form.

10 Claims, No Drawings

{ 3,944,662 }

NON-VOLATILE SLOW-RELEASE PESTICIDAL GENERATORS

CROSS-REFERENCE TO RELATED APPLICATIONS

This is a continuation-in-part of U.S. application Ser. No. 244,942, filed Apr. 17, 1972, now abandoned.

BACKGROUND OF THE INVENTION

This invention relates to slow-release pesticide generators. More particularly, this invention relates to slow-release pesticide generators comprising a non-volatile vinyl phosphate pesticide dispersed in a plasticized thermoplastic resin wherein the pesticide migrates onto the resin surface and is maintained thereon in a certain crystalline form. These generators are useful in the control of non-vertebrate pests and particularly in the control of ectoparasites such as fleas and ticks on warm-blooded animals.

DESCRIPTION OF THE PRIOR ART

It is known in the art to prepare slow-release pesticide generators in which a resinous substance is mixed with a volatile pesticide to form a composition that will slowly release the volatile pesticide into the surrounding atmosphere over an extended period of time. (See U.S. Pat. No. 3,318,769). These generators function by the pesticide slowly being released from the generator and filling the surrounding atmosphere with a vaporous concentration of pesticide that is lethal to the pest but is innocuous to warm-blooded animals.

These slow-release compositions have been developed for numerous uses. The most common use consists in placing the slow-release product in the form of a strip in an enclosed atmosphere, such as in a room, and allowing the concentration of vaporous pesticide to build up to the point at which pests are killed but other life is not harmed.

Another use widely found for the slow-release compositions is as an ectoparasiticide. Collars made of the resinous generators are placed around the neck of the animal to be treated or a medallion may be hung from a collar on the animal. The pesticide vapor released from these products functions well to protect the animal from pests such as fleas and ticks over an extended period of time.

These prior art products contain as an active ingredient volatile phosphate esters which are toxic to warm-blooded animals at sufficiently high concentrations. When formulated into the slow-release resinous matrix and used as directed, the concentration of volatile pesticide in the air is low and presents no safety hazard.

However, in spite of the efficacy and safety of these prior art products, there are certain so-called "sensitive" animals who have a tendency to develop skin irritations in the vicinity of the point of contact with the volatile pesticide slow-release matrix. This is particularly true with cats. For example, in the case of collars the irritation has been found to develop in the area of the neck of the animal.

It would be highly desirous to develop a slow-release composition which would function effectively as an ectoparasiticide and yet be virtually free from the toxicity and skin irritation problems of prior art products.

BRIEF SUMMARY OF THE INVENTION

There has now been found a new slow-release pesticide generator which eliminates the objections to the prior art products and yet retains a high degree of efficacy against pests especially when used to rid animals of certain ectoparasites. Whereas the prior art slow-release products operate by using a volatile pesticide, it has now been found that a particular non-volatile pesticide may be incorporated into a resinous matrix to form a product which is both efficacious and has a high degree of safety.

In particular, it has been discovered that the $\beta$-isomer of 2-chloro-1-(2,4,5-trichlorophenyl)-vinyl dimethyl phosphate may be incorporated into a thermoplastic resin to form a product which slowly releases the phosphate to the surface of the thermoplastic resin in a particular crystalline form, and that the crystalline form can be modified to yield a pesticide generator which is stable during storage, yet highly efficacious in use.

DETAILED DESCRIPTION OF THE INVENTION

The $\beta$-2-chloro-1-(2,4,5-trichlorophenyl)-vinyl dimethyl phosphate is more pesticidally active than the corresponding $\alpha$-isomer and has a very low mammalian toxicity. This has been reported, for example, by Whetstone et al, J. Agricultural Food Chemistry, Volume 14, pages 352–356, July-August 1966. The acute oral mammalian toxicity ($LD_{50}$ in milligrams per kilogram of body weight, male rats) is 4000 to 5000 for the $\beta$-isomer as compared to an $LD_{50}$ of from 56-80 for the unformulated liquid vinyl phosphates typically used in the prior art. Conventionally, the $\beta$-2-chloro-1-(2,4,5-trichlorophenyl)-vinyl dimethyl phosphate has been formulated in dusts, wettable powders, water dispersable suspensions and emulsifiable concentrates. The possibility of incorporating dimethyl 1-(2,4,5-trichlorophenyl)-2-chlorovinyl phosphate into a thermoplastic resin is disclosed in British Pat. No. 1,040,553, but to our knowledge this has never been accomplished heretofore.

It has now been found that when $\beta$-2-chloro-1-(2,4,5-trichlorophenyl)-vinyl dimethyl phosphate is incorporated into plasticized thermoplastic resin that it migrates to the surface of the resin and crystallizes thereon in one or more distinct crystalline forms herein called "polymorphs." It has further been found that the properties of the resulting compositions are significantly affected by the particular crystalline form or polymorph maintained on the surface of the composition, and that it is possible to vary the properties of the compositions in an advantageous manner by modifying the crystalline structure as hereinafter explained.

Optical microscopy and fusion studies on $\beta$-2-chloro-1-(2,4,5-trichlorophenyl)-vinyl dimethyl phosphate and plasticized thermoplastic resin compositions containing it now indicate that this compound can occur in at least three crystalline or polymorphic forms hereinafter designated as "Polymorph I", "Polymorph II" and "Polymorph III". Polymorph I is the most stable form having platelet-like crystals melting at about 95°–98°C. Polymorph II is a metastable form having needle-like crystals and shows a phase transformation or melting point at 44°–54°C. Polymorph II may convert to Polymorph I or to Polymorph III which in turn converts to Polymorph I by phase transition (p.t.) at 76°–81°C. In some cases a melt may skip Polymorph II and directly form Polymorph III or I or a mixture of both. These transformations may be summarized by the following diagram

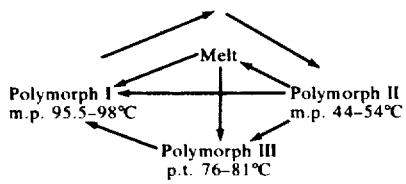

Thermoplastic resin compositions containing β-2-chloro-1-(2,4,5-trichlorophenyl)-vinyl dimethyl phosphate have now been found in which either Polymorph I or Polymorph II crystals may be maintained upon the surface of a thermoplastic resin. The compositions containing Polymorph I crystals on the surface are more stable and therefore less subject to bloom and have a longer storage or shelf life. On the other hand, compositions in which Polymorph II crystals are present on the surface are more toxic to insects and constantly release the toxicant from within the resin matrix.

Compositions containing Polymorph II on the surface of the thermoplastic resin can be obtained employing conventional methods of preparation. For example, such compositions can be prepared by mechanical mixing of the powdered ingredients which are heated to bring about a homogeneous melt which can be cast, extruded, injected or molded into the desired shape such as sheets, strips, films, rods, granules, pellets and the like. When the cast, extruded, injected or molded article is cooled to ambient conditions, the β-chloro-1-(trichlorophenyl)-vinyl dimethyl phosphate migrates to and "blooms" onto the surface of the resin matrix in the form of needle-like Polymorph II crystals and, unless prevented, will continue to bloom in this form until the β-chloro-1-(trichlorophenyl)-vinyl dimethyl phosphate initially present in the thermoplastic matrix has been substantially depleted. An important advantage of the compositions of the invention lies in the discovery that further bloom or crystal formation which is undesirable under certain conditions, such as during storage, can be substantially prevented or inhibited by conversion of the Polymorph II crystals to Polymorph I.

The formation of Polymorph I crystalline structure on the surface of the resin generator is accomplished by "curing" or heating the Polymorph II-containing pesticide generator as prepared above at an elevated temperature for a time sufficient to bring about the conversion of the polymorphic forms. This subsequent separate heating step may be accomplished by conventional means such as heating the Polymorph II-containing resin product in an oven. Other means such as microwave curing or subjecting to infrared light might also be used. Typically the conversion of Polymorph II to Polymorph I crystals will take place if the compositions are heated at about 130° to 150°F for about 30 minutes to 2 hours. Generally, the thicker the layer of Polymorph II crystals initially on the surface, the longer the heating period or the higher the temperature required. For best results the resin product should contain a uniform Polymorph II crystal bloom before heating.

As previously mentioned, the conversion of Polymorph II to Polymorph I crystals is an important aspect of the present invention in that the continuous blooming of Polymorph II crystals under certain conditions, such as during storage, is undesirable since it can lead to the loss of a considerable portion of the β-chloro-1-(trichlorophenyl)-vinyl dimethyl phosphate toxicant from the matrix while the product is "on the shelf". The conversion of the Polymorph II crystals to Polymorph I by the additional heating step (i.e., the further heating step after preparation of the initial resin product) substantially prevents or inhibits crystal bloom during storage thereby providing a storage stable product. This unexpected result is believed due to the fact that the Polymorph I crystals so formed are platelet-like in shape and are closely knit or overlap each other as shingles on a roof. In this formation migration of the phosphate toxicant from within the resin matrix to the surface is substantially prevented and the compositions can be stored over extended periods of time without significant loss of toxicant. To induce or start the blooming process again, all one has to do is to rub, wipe, abrade or otherwise disturb the surface of the resin generator, e.g., by stretching, to break or remove the Polymorph I crystalline structure whereupon the Polymorph II crystals start to bloom out again. A comparison of pesticidal toxicity has demonstrated that Polymorph II is more toxic than Polymorph I, hence it is desirable that Polymorph II bloom be resumed for maximum toxic effect.

In addition to polymorphism, the pesticidal toxicity of the crystals is determined somewhat by the crystal size. Smaller crystals present a greater surface area per unit weight than larger ones. Moreover, smaller crystals more uniformly cover a given area than larger crystals, thereby increasing the likelihood that a pest within that area will come in contact with the crystals. It therefore follows that smaller crystals are preferred as being pesticidally more active.

As mentioned above, the β-chloro-1-(2,4,5-trichlorophenyl)-vinyl dimethyl phosphate in a conventionally prepared resin composition diffuses to the surface of the resin matrix and crystallizes in the form of Polymorph II crystals. The precise state of the phosphate ester remaining in the thermoplastic matrix is not known but it is believed to be in solution. The crystallization of β-2-chloro-1-(trichlorophenyl)-vinyl dimethyl phosphate apparently follows the first portion of Ostwald's Rule that if a substance can exist in more than one form, the least stable is formed first, and changes ultimately into the more stable. Surprisingly, however, instead of converting to the more stable form, Polymorph II remains on the surface of the plastic matrix for a prolonged period of time.

The mode of action of the composition of the invention is different from that of the prior art vapor producing slow-release products. The β-2-chloro-1-(2,4,5-trichlorophenyl)-vinyl dimethyl phosphate diffuses from within the thermoplastic matrix to the surface where it crystallizes or "blooms" out onto the surface as microcrystalline particles of Polymorph II which may grow from a few molecules to 100–300 microns in size depending upon the rate of diffusion to the surface and the rate at which the "bloom" is removed from the surface of the resin. The pest to be controlled must be brought into physical contact with the active ingredient. In the case of protecting a pet against ectoparasites, this is accomplished by forming the resinous mixture into the form of a collar to be placed around the animal's neck. Since fleas and ticks tend to concentrate in or migrate through the area of the neck of the animal, some are brought into contact with the active phosphate ester on the surface of the collar and killed. It is also known that, due to the movement of the animal, the microcrystals are rubbed or wiped from the surface of the collar and spread into the fur of the animal where they continue to control ectoparasites. Whether the crystals removed from the surface of the resinous substrate remain as Polymorph II or convert to Polymorph I is not known. However, the invention is not limited to the use of any one polymorph as all polymorphs are biologically active. Moreover, the crystals blooming onto the surface of the resinous collar and falling into the fur of the animal are microcrystalline in size and even if in the form of Polymorph I are more active than crystals produced by conventional methods.

Any plasticized thermoplastic resin which is compatible with β-2-chloro-1-(2,4,5-trichlorophenyl)-vinyl dimethyl phosphate and capable of releasing pesticidally effective amounts of this toxicant to the surface of the resin may be used. Typical of such resins are the vinyl resins, polyvinyl halides such as polyvinyl chloride; polyvinyl esters; polyvinylidene compounds such as polyvinylidene chloride; synthetic and natural elastomers, such as *Hevea brasiliensis*, cis-1,4-polyisoprene, polybutadiene, SBR rubber, and copolymers of such rubbers; cellulose plastics, such as cellulose acetate, cellulose butyrate, cellulose nitrate and the like. Because the primary use envisioned for the compositions of the invention is as a collar to control ectoparasites on pets or other animals, the resinous material should be sufficiently flexible to be used for that purpose. For this reason, thermoplastic materials such as polyvinyl chloride and copolymers thereof are preferred. In general thermoplastic resin concentrations may vary from about 20 to 70% by weight of the total composition.

The plasticizers which may be used are those conventionally used in the plasticization of thermoplastic resins such as polyvinyl chloride (PVC). These plasticizers are generally of two types, i.e., phosphate esters and esters of polybasic carboxylic acids. The phosphate esters are preferably relatively non-volatile and inert. These compounds are described by the structure

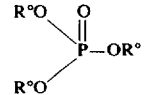

where R° can be the same or different and is a hydrocarbon radical selected from the group consisting of alkyl, aryl, aralkyl, and alkaryl preferably having at least four carbon atoms. These esters are virtually non-volatile but impart excellent plasticized properties to the resulting composition. Because of their similar composition they are readily compatible with the β-2-chloro-1-(2,4,5-trichlorophenyl)-vinyl dimethyl phosphate. Typical phosphate esters include the triaryl phosphates, such as tricresyl phosphate, triphenyl phosphate, tri(p-tert-butylphenyl) phosphate, tri(-biphenylyl) phosphate, o-biphenylyl diphenyl phosphate, and cresyl diphenyl phosphate; the trialkyl phosphates such as tri-n-butyl phosphate, tri-2-ethyl-hexyl phosphate, tri-n-octyl phosphate and tri-lauryl phosphate, tri-butoxyethyl phosphate; and such mixed phosphates as 2-ethyl-hexyl diphenyl phosphate and the like. Typical of the esters of polybasic carboxylic acids are phthalate esters, such as dioctyl phthalate, didecyl phthalate, ditridecyl phthalate, dibutyl phthalate, diphenyl phthalate, dicyclohexyl phthalate, dimethyl phthalate and dihexyl phthalate; the sebacates, such as dibutyl sebacate, dipentyl sebacate, n-butyl benzyl sebacate and dibenzyl sebacate; the adipates, such as dioctyl adipate, dicapryl adipate, diisobutyl adipate and dinonyl adipate, and the citrates such as tributyl citrate. Because of their availability, dioctyl adipate, dioctyl phthalate and tricresyl phosphate are most commonly used.

The compositions of the invention may vary depending upon the components used. The β-2-chloro-1-(2,4,5-trichlorophenyl)-vinyl dimethyl phosphate may comprise from about 3 to 30% by weight of the total composition with concentrations of about 5 to 20% by weight being preferred. When used to formulate animal collars, optimum concentration of the active phosphate pesticide is in the neighborhood of 10% by weight or say from 7 to 13% by weight.

The amount of plasticizer to use will be that amount required to plasticize the resin to the required degree of flexibility. The plasticizer also contributes to the rate at which the β-2-chloro-1-(2,4,5-trichlorophenyl)-vinyl dimethyl phosphate migrates to the surface of the composition. Different plasticizers and amount of plasticizer influence this rate of migration. Higher concentrations of plasticizer tend to raise the rate of phosphate migration to the surface. The maximum rate of migration seems to occur when using plasticizers having a solubility parameter of about 8.4 to 8.7 Hildebrand units. In general plasticizer concentrations may vary from about 25 to 50% by weight of the total composition with amounts of 30 to 40% by weight being preferred.

Other ingredients such as stabilizers, attractants, dyes, fillers, odorants or other biocides may also be used in the compositions without departing from the scope of this invention. Useful additives such as carbon black, titanium dioxide and other insoluble pigments and fillers, which when added in small amounts, i.e., 1% w or less serves to color the resinous mixture.

The migration rate of β-2-chloro-1-(2,4,5-trichlorophenyl)-vinyl dimethyl phosphate to the surface of a slow-release generator having a resin matrix is only partially dependent upon the plasticizer used. Other factors influencing such migration include the concentration of the phosphate in the matrix, the geometry of the slow-release generator and the extent to which the bloom or crystals are removed from the surface of the generator. Obviously, less bloom on the surface will result in faster migration of the phosphate to the surface. As the bloom first appears, the crystals are very small in size, perhaps only a few molecules, but if the crystals are not removed they continue to grow until they are perhaps a few hundred microns. The larger and more numerous the crystals become, the more migration of the phosphate to the surface becomes inhibited.

The pesticide composition of this invention is effective in killing invertebrate pests, including various ticks, spiders, mites, and insects by subjecting them to the compositions of the invention. These compositions can be used as granules or pellets and placed in the soil wherein the slow sustained release of the phosphorus ester results in the control of various soil pests such as cutworms, rootworms, etc. The compositions can also be formed as sheets, rods or films and placed in barns or other areas usually inhabited by flies. When used for this purpose, incorporation of a pheromone or other atttractant into the composition will act to draw the flies to the composition. The major use anticipated, as previously stated, is the formation of the compositions into collars to be placed around the neck of an animal such as a dog or cat, for the control of ectoparasites on the animal.

The invention is illustrated by the following examples.

EXAMPLE I

Pet collars containing 11% w of $\beta$-2-chloro-1-(2,4,5-trichlorophenyl)-vinyl dimethyl phosphate, 34% w of a plasticizer, 53.5% w polyvinyl chloride and 1.5% w of a PVC stabilizer were prepared by injection molding. Various plasticizers were used to demonstrate the effect the plasticizer has on the release rate of toxicant phosphate ester from the resin matrix. The release rate was determined by weight loss. The collars were all exposed in a fume hood maintained at 70°–75°F annd 30–50% relative humidity, and weight loss was determined by periodically wiping the collar and weighing the collar. The results are recorded in Tables I and II.

|  | A | B | C |
|---|---|---|---|
| $\beta$-2-chloro-1-(2,4,5-trichlorophenyl)-vinyl dimethyl phosphate | 10 | 10 | — |
| Di(2-ethylhexyl) adipate | 34.5 | 34.5 | 38.2 |
| Polyvinyl chloride resin | 54 | 53 | 60.1 |
| PVC Stabilizers | 1.5 | 1.5 | 1.7 |
| Styrene-Butadiene-Styrene Block Copolymer | — | 1 | — |

The collars (10 of each formulation) were sealed in metal foil pouches and sent to a commercial testing laboratory. At the laboratory, the collars were wiped to remove Polymorph I from the surface, and placed around the neck of mixed breed dogs infected with *C. felis*. The dogs were grouped in separate units according to collar formulation. Each group was confined in a chain link run during the night in a ventilated building having a concrete slab floor. Self-feeding and watering facilities were provided in each run.

During the day, each group of dogs was placed in a separate run outside the building. These runs were partitioned on their common sides with solid plywood

TABLE I

Cumulative Weight[a] of $\beta$-2-Chloro-1-(2,4,5-Trichlorophenyl)-Vinyl Dimethyl Phosphate Found on Surface of Collars, Grams

| Days | Tricresyl Phosphate | Tributoxy-ethyl Phosphate | Trioctyl Phosphate | Monocresyl diphenyl Phosphate | 2-Ethylhexyl diphenyl Phosphate | Tributyl Phosphate |
|---|---|---|---|---|---|---|
| 2 | .027 | .206 | .113 | .056 | .114 | .023 |
| 4 | .039 | .334 | .210 | .090 | .183 | .370 |
| 7 | .058 | .476 | .331 | .118 | .255 | .527 |
| 10 | .077 | .607 | .442 | .147 | .317 | .659 |
| 17 | .113 | .806 | .621 | .208 | .433 | .875 |
| 24 | .133 | .952 | .766 | .236 | .518 | 1.035 |
| 32 | .156 | 1.100 | .906 | .275 | .604 | 1.161 |

[a] Determined by periodically wiping of collar following exposure at 70–75°F, 30–50% relative humidity in fume hood.

TABLE II

Cumulative Weight[a] of $\beta$-2-Chloro-1-(2,4,5-Trichlorophenyl)-Vinyl Dimethyl Phosphate Found on Surface of Collars, Grams

| Days | Dioctyl Phthalate | Didecyl Phthalate | Ditridecyl Phthalate | Dibutyl Phthalate | * | * |
|---|---|---|---|---|---|---|
| 2 | .067 | .064 | .059 | .100 | .088 | .091 |
| 5 | .133 | .136 | .116 | .202 | .208 | .202 |
| 7 | .165 | .171 | .137 | .255 | .278 | .282 |
| 9 | .196 | .203 | .169 | .299 | .340 | .343 |
| 12 | .240 | .241 | .200 | .350 | .409 | .408 |
| 15 | .269 | .275 | .225 | .396 | .463 | .469 |
| 23 | .340 | .343 | .282 | .495 | .590 | .585 |

[a] Determined by periodically wiping of collar following exposure at 70–75°F, 30–50% relative humidity in fume hood.
*Phthalate esters of mixed straight chained alcohols.

EXAMPLE II

Dog collars were made by mixing the raw materials together as a melt and by injection molding forming them into collars. Collars A and B were heat-treated at 150°F for four hours after preparation to convert the $\beta$-2-chloro-1-(2,4,5-trichlorophenyl)-vinyl dimethyl phosphate from Polymorph II to Polymorph I to control bloom on the surface of the collar during storage. The formulation of the collars (% weight) was as follows:

sheeting 6 feet in height. Sand was placed in the outside runs to simulate a more natural environment for the fleas.

Approximately 120 *C. felis* pupae per dog were placed in the outside runs each week. The weather during the course of the trail was favorable for natural emergence of the adult fleas. Counting of the fleas on the dogs was done 3 times weekly. Two attendants performed the counting, one on each side of the dog. Each had a fine tooth comb to turn the hair. Counting progressed from posterior to anterior extremities of the dog. The results are as follows in Table III.

TABLE III

| | AVERAGE FLEA INFESTATION Cumulative Days | | | | | | | | | | | | | | | | | | | |
|---|---|---|---|---|---|---|---|---|---|---|---|---|---|---|---|---|---|---|---|---|
| Collar | 0[a] | 2 | 4[a] | 7 | 9 | 11[a] | 14 | 16 | 18[a] | 21 | 23 | 25[a] | 28 | 32[a] | 34 | 37 | 39[a] | 42 | 44 | 46[a] | 49 |
| A | 0 | .1 | 0 | 0 | 0 | 0 | .2 | 0 | 0 | 0 | 0 | 0 | .3 | 0 | 0 | .1 | 0 | .5 | .3 | .7 | .8 |
| B | 0 | 0 | 0 | 0 | 0 | 0 | 0 | 0 | 0 | 0 | 0 | 0 | .2 | 0 | 0 | 0 | 0 | .3 | .2 | .1 | .3 |
| C Control | 8.2 | 6.0 | 10.4 | 7.4 | 4.4 | 3.8 | 11.3 | 7.5 | 7.6 | 8.3 | 6.7 | 6.1 | 6.3 | 7.1 | 9.4 | 8.0 | 7.7 | 9.7 | 11.1 | 11.8 | 13.1 |

| | Cumulative Days | | | | | | | | | | | | | | | | | | |
|---|---|---|---|---|---|---|---|---|---|---|---|---|---|---|---|---|---|---|---|
| Collar | 51 | 53[a] | 56 | 58 | 60[a] | 63 | 65 | 67[a] | 70 | 72 | 74[a] | 77 | 79 | 81[a] | 84 | 86 | 88[a] | 90 | 92 |
| A | .3 | .1 | .4 | 0 | .4 | 1.1 | 1.0 | .8 | .8 | 1.0 | 1.0 | .5 | .6 | 1.0 | .8 | 1.0 | .9 | 1.5 | 2.4 |
| B | 0 | .1 | 0 | .1 | 0 | .3 | .1 | .6 | .4 | .6 | .7 | .7 | .8 | 1.2 | .6 | .5 | .8 | 1.1 | 1.2 |
| C Control | 11.3 | 12.8 | 12.3 | 14.1 | 12.4 | 14.4 | 11.6 | 11.7 | 11.1 | 13.1 | 14.1 | 11.8 | 12.8 | 14.0 | 11.9 | 10.9 | 9.4 | 19.0 | 17.2 |

[a]Date infested; counts prior to reinfestation at weekly intervals.

The results show the effectiveness of collars containing β-2-chloro-1-(2,4,5-trichlorophenyl)-vinyl dimethyl phosphate as compared to a control group wearing a placebo collar. No gross symptons on toxicity were noted in the dogs wearing the collar from formulations A and B. Dogs wearing C collars showed a progressive deterioration of their general health, particularly hair, coat and skin lesions due to the excessive scratching and mutilation caused by the flea burden they carried. Irritation around the necks of the dogs were minimal and apparently due to pressure mechanically produced by the collars.

EXAMPLE III

Cat collars were made in a manner similar to those made in Example II. The collars had the following formulation:

| | A | B | C | D |
|---|---|---|---|---|
| β-2-chloro-1-(2,4,5-trichloro-phenyl)-vinyl dimethyl phosphate | 5 | 10 | 20 | — |
| Di(2-ethylhexyl adipate) | 39.5 | 34.5 | 30 | 33.0 |
| Polyvinyl chloride | 54.0 | 54 | 48.5 | 65.5 |
| PVC Stabilizers | 1.5 | 1.5 | 1.5 | 1.5 |

Six collars of formulation D (Placebo collars) and five each of formulations A, B and C sealed in metal foil were sent to a commercial testing laboratory. At the laboratory the collars were wiped to remove Polymorph I and the collars were placed on cats. Each cat was infested with 100 fleas. At the end of 7 days each cat would be thoroughly checked and live fleas found counted. The cat would thereupon be reinfested with 100 fleas and the procedure repeated. The tests continued for 16 weeks with the results being recorded in Table IV.

During the tests, one cat wearing a collar of formulation B died. Analysis of the collar showed it to contain the same ingredients as the other B collars. It was not believed that the collar contributed to the death of the cat. The data in the table clearly indicate the effectiveness of various concentrations of β-2-chloro-1-(2,4,5-trichlorophenyl)-vinyl dimethyl phosphate in reducing flea infestation.

EXAMPLE IV

The influence of particle size and the relative toxicity of the polymorphs of β-2-chloro-1-(2,4,5-trichlorophenyl)-vinyl dimethyl phosphate are illustrated below. An approximate 5% w mixture was made by mixing together 5.4% of toxicant, 34.6% w of dioctyl adipate as plasticizer, 58.5% w of polyvinyl chloride and 1.5% w of PVC stabilizer. This dry mixture was extruded through appropriate dies to form either a film 2–4 mils thick or a ⅛ inch diameter strand. The film was supported on 6 inch diameter embroidery hoops and the strand was tightly coiled over a 5 × 5 inch aluminum plate and secured with copper wire. The specimens were stored for 5 days at about 73°F.

Polymorph I was prepared by heating the resin formulations at 131°F for 1 hour. Polymorph I was also prepared by spraying a benzene solution of toxicant on a glass plate.

Housefly toxicity was determined by exposing 50 flies under a 4 inch diameter screened cage for one hour to the toxicant and mortality readings made 24 hours later. Results are recorded below in Table V.

TABLE V

| Poly-morph | Crystal Size Range (microns) | Toxicant Concentration mg/ft$^2$ | % Mortality to Housefly |
|---|---|---|---|
| I[a] | 15–45 | 10 | 74 |
| I[b] | 150–300 | 125 | 88 |
| II[c] | 100–300 | 10 | 84 |

[a]Residue from benzene solution sprayed on glass.
[b]Crystals bloom from ⅛ inch diameter PVC strand, and converted to Polymorph I
[c]Crystals bloom from 2–4 ml thick PVC film.

TABLE IV

| | AVERAGE FLEA INFESTATION Weeks | | | | | | | | | | | | | | | |
|---|---|---|---|---|---|---|---|---|---|---|---|---|---|---|---|---|
| Collar | 1 | 2 | 3 | 4 | 5 | 6 | 7 | 8 | 9 | 10 | 11 | 12 | 13 | 14 | 16 |
| A | 3.8 | 5.4 | 10.0 | 6.8 | 7.2 | 10.6 | 7.4 | 3.0 | 3.2 | 6.6 | 5.2 | 6.8 | 5.0 | 7.2 | 8.6 |
| B | 0.2 | 0 | 0 | 0 | 0 | 0 | 0.5 | 1.0 | 2.3 | 3.0 | 1.3 | 1.5 | 3.0 | 1.5 | 5.3 |
| C | 0.2 | 0 | 0 | 0 | 0 | 0 | 0 | 0 | 0 | 0.4 | 0 | 1.0 | 1.0 | 0.6 | 0.6 |
| D Control | 16.0 | 9.2 | 19.8 | 16.8 | 16.0 | 31.7 | 22.3 | 26.0 | 35.7 | 53.8 | 61.2 | 51.3 | 55.3 | 44.8 | 48.2 |

The results indicate that at similar crystal sizes the concentration of Polymorph I must be greater than Polymorph II to obtain the same mortality counts.

EXAMPLE V

Compositions of β-2-chloro-1-(2,4,5-trichlorophenyl)-vinyl dimethyl phosphate with plasticized polymers other than PVC were prepared by mixing the ingredients and then heated by molding, extrusion or in a Brabender mixer. The cooled compositions were allowed to set for several days and then examined for bloom on the surface. All compositions showed bloom. In each of the mixtures listed in Table VI, the plasticizer was dioctyl phthalate (DOP).

TABLE VI

| Polymer | Polymer % w | Plasticizer % w | β-2-chloro-1-(2,4,5-trichlorophenyl)-vinyl dimethyl phosphate % w |
|---|---|---|---|
| Acrylonitrile-Butadiene Styrene Polymer | 55 | 35 | 10 |
| Acrylonitrile elastomer Polyvinylacetate copolymer | 65 | 25 | 10 |
| Polyvinylacetate copolymer | 40 | 50 | 10 |

EXAMPLE VI

The effect of heat treating (annealing) on the storage stability of the present compositions is illustrated below. Two lots of pet collars were prepared by mixing together as a melt 11.0% of β-2-chloro-1-(2,4,5-trichlorophenyl)-vinyl dimethyl phosphate, 34.0% w dioctyl adipate as plasticizer, 53.2% w polyvinyl chloride, 1.5% w PVC stabilizer and 0.3% w pigment, and injection molding the resultant mixture into the form of pet collars. The injection molded collars were 21 inches long, weighed 21.7 grams and contained approximately 10.0% β-2-chloro-1-(2,4,5-trichlorophenyl)-vinyl dimethyl phosphate, i.e., 2.17 g./collar. A portion of the injection molded collars, after a uniform layer of crystal bloom had formed, were heat treated in an oven maintained at 150°F for 4 hours which resulted in the powdery crystal bloom disappearing, and after cooling slowly to room temperature, the appearance of the flat, shiny platelet-like Polymorph I crystals. The heat treated and the untreated collars were stored in individual sealed pouches under ambient conditions, i.e., approximately 70°-74° F. Periodically one or more treated and untreated collars were removed from storage and the amount of β-2-chloro-1-(2,4,5-trichlorophenyl)-vinyl dimethyl phosphate which crystallized on the surface determined. These results are tabulated below. The amount of toxicant which crystallized during storage is expressed as percent of the initial toxicant concentration.

TABLE VII

TOXICANT CRYSTALLIZATION DURING STORAGE
% of Toxicant Crystallized from Composition

| Storage Time in Package | Heat Treated Collar | Untreated Collar |
|---|---|---|
| 1 week | 0.8 | 3.3 |
| 17 days | 0.9 | 6.6 |
| 1 month | 1.2 | 7.3 |
| 2 months | 1.8 | 8.8 |
| 3 months | 1.8 | 11.5–18.4 |
| 6 months | 2.1 | 12.9–18.4 |
| 1 year | 2.8–5.5 | 32.8–49.8 |

The foregoing results indicate that the collars which were heat treated to form the platelet-like Polymorph I crystals on their surface were significantly more stable in storage than untreated collars which lost a large percentage of their available toxicant during the one year storage period.

We claim as our invention:

1. A storage stable, slow-release pesticide composition for controlling invertebrate pests consisting essentially of a pesticidally effective amount of from about 3% to 30% by weight of the total composition of β-2-chloro-1-(2,4,5-trichlorophenyl)-vinyl dimethyl phosphate dispersed in a matrix of plasticized thermoplastic resin compatible with said phosphate and capable of releasing a pesticidally effective amount of said phosphate onto the surface of said composition, said composition being characterized by having on the surface thereof a polymorphic form of β-2-chloro-1-(2,4,5-trichlorophenyl)-vinyl dimethyl phosphate further characterized by a platelet-like crystalline structure and a melting point of 95°–98°C, which crystalline structure inhibits migration of further quantities of β-2-chloro-1-(2,4,5-trichlorophenyl)-vinyl dimethyl phosphate from within the matrix onto the surface thereof.

2. A composition according to claim 1 wherein the composition contains from about 20 to 70% w of thermopastic resin and from about 25 to 50% of plasticizer for said resin.

3. A composition according to claim 1 wherein the plasticized thermoplastic resin is plasticized polyvinyl chloride.

4. A composition according to claim 2 wherein the thermoplastic resin is polyvinyl chloride.

5. A method for preventing the release of β-2-chloro-1-(2,4,5-trichlorophenyl)-vinyl dimethyl phosphate from within, onto the surface of a solid composition consisting essentially of a pesticidally effective amount of from about 3 to 30% by weight of the total composition of said β-2-chloro-1-(2,4,5-trichlorophenyl)-vinyl dimethyl phosphate dispersed in a matrix of plasticized thermoplastic resin compatible with said phosphate and capable of releasing a pesticidally effective amount of said phosphate onto the surface of said composition, said composition having on the surface thereof a polymorphic form of β-2-chloro-1-(2,4,5-trichlorophenyl)-vinyl dimethyl phosphate characterized by a needle-like crystalline structure, which comprises subjecting said composition to an elevated temperature for a period of time sufficient to convert substantially all of said β-2-chloro-1-(2,4,5-trichlorophenyl)-vinyl dimethyl phosphate in said needle-like polymorphic form to a polymorphic form characterized by a platelet-like crystalline structure and a melting point of 95°–98°C, the presence of said latter polymorphic form serving to inhibit the migration of further quantities of β-2-chloro-1-(2,4,5-trichlorophenyl)-vinyl dimethyl phosphate from within the matrix onto the surface of said composition.

6. A method of inducing the release of β-2-chloro-1-(2,4,5-trichlorophenyl)-vinyl dimethyl phosphate from within, onto the surface of a storage stable, slow-release pesticide composition consisting essentially of a pesticidally effective amount of from about 3% to 30% by weight of the total composition of said β-2-chloro-1-(2,4,5-trichlorophenyl)-vinyl dimethyl phosphate dispersed in a matrix of plasticized thermoplastic resin compatible with said phosphate and capable of releasing a pesticidally effective amount of said phosphate onto the surface of said composition, the composition having on its surface said β-2-chloro-1-(2,4,5-trichlorophenyl)-vinyl dimethyl phosphate in a polymorphic form characterized by a platelet-like crystalline structure and a melting point of 95°–98°C, which method comprises disturbing the surface of said composition so as to remove said β-2-chloro-1-(2,4,5-trichlorophenyl)-vinyl dimethyl phosphate in said polymorphic form therefrom, thereby permitting the migration of further amounts of β-2-chloro-1-(2,4,5-trichlorophenyl)-vinyl dimethyl phosphate from within said composition.

7. A method according to claim 6 wherein the plasticized thermoplastic resin in said composition is plasticized polyvinyl chloride.

8. A method of controlling invertebrate pests which comprises subjecting said pests to a pesticidally effective amount of the composition of claim 1.

9. A method of controlling ectoparasites on dogs and cats which comprises
   a. preparing the composition of claim 1 in the form of a collar,
   b. disturbing the surface of said collar to remove the platelet-like crystals of β-2-chloro-1-(2,4,5-trichlorophenyl)-vinyl dimethyl phosphate present thereon thereby permitting a further amount of said phosphate insecticide to migrate from within the collar onto the surface thereof, and
   c. attaching said collar to a dog or cat whereupon the phosphate pesticide present on the surface of said collar is rubbed or wiped therefrom by movement of the dog or cat and spreads into the fur of the animal thereby controlling ectoparasites.

10. A method of controlling ectoparasites on dogs or cats according to claim 9 wherein the composition prepared in the form of a collar is the composition of claim 3.

* * * * *